United States Patent [19]

Chiang

[11] Patent Number: 4,933,450

[45] Date of Patent: Jun. 12, 1990

[54] PREPARATION OF 2-AMINOTRIAZINES

[75] Inventor: George C. Chiang, Wilmington, Del.

[73] Assignee: E.I. du Pont de Nemours and Company, Wilmington, Del.

[21] Appl. No.: 373,073

[22] Filed: Jun. 29, 1989

[51] Int. Cl.$^5$ ............................................. C07D 251/16
[52] U.S. Cl. ..................................... 544/194; 544/219
[58] Field of Search ................................. 544/219, 194

[56] References Cited

U.S. PATENT DOCUMENTS 2,418,476  4/1947  Nagy et al. .............................. 23/78

FOREIGN PATENT DOCUMENTS 70296    12/1969  German Democratic Rep. .
71768     3/1970  German Democratic Rep. .
252374   12/1987  German Democratic Rep. .
1067695   5/1967  United Kingdom .
1180346   2/1970  United Kingdom .

OTHER PUBLICATIONS

Rembarz et al., J. fur Pract. Chemie 1969 (311) 889–892, Chemical Abstracts entry 66905s, vol. 72, (1970).
Rembarz et al., Wiss. Z. Univ. Rostock. Math.-Naturwiss. Reihe, 1972, 21(2) 93–100, Chemical Abstracts, vol. 79: 31443g (1972).
Kohler, Z. Anorg. Allg. Chemie, 381 (5–6), 237 (1964).
Rembarz et al., Wiss. Z. Univ. Rostock, Math.-Naturwiss. Reihe, 1972, 21(2), 113–117; Chemical Abstracts, vol. 79, entry 18679u (1973).

Primary Examiner—John M. Ford

[57] ABSTRACT

A metal.dicyanimide.ligand complex having the formula $M[N(CN)_2]_2.ligand_2$ wherein M is Zn, Cu, Mg, Ca, Fe, Al or Si and ligand is a group capable of donating a pair of electrons, a process for its preparation, and its use in the preparation of aminotriazines is disclosed.

10 Claims, No Drawings

PREPARATION OF 2-AMINOTRIAZINES

BACKGROUND OF THE INVENTION

The present invention relates to the preparation of aminotriazines which are useful in the production of commercial herbicides.

U.S. Pat. No. 2,418,476 of Nagy et al. discloses the synthesis of zinc bis(dicyanimide) $Zn[N(CN)_2]_2$. This insoluble compound can be converted to a coordination complex, zinc bis(imino-bis-carbimic acid methyl ester) by refluxing in methanol, disclosed in Rembarz et al., J. fur Pract. Chemie 1969 (311) 889-892. This reaction produces the coordination complex in a yield of about 50% to 75% along with some insoluble materials. The coordination complex is then converted to 2-methyl-4,6-dimethoxy-1,3,5-triazine.

East German Pat. Nos. 70,296 of Rembarz et al. and 71,768 of Rober et al., Great Britain Patent No. 1,180,346 of Rober et al., and Rembarz et al., Wiss. Z. Univ. Rostock. Math.-Naturwiss. Reihe, 1972, 21(2) 93-100 each discloses similar transformations of zinc bis(dicyanimide) to zinc bis(imino-bis-carbimic acid methyl ester) to 2-methyl-4,6-dimethoxy-1,3,5-triazine.

Kohler, Z. Anorg. Allg. Chemie., 331 (5-6), 237, (1964) discloses the preparation of metal bis(dicyanimide)bis(pyridine), $M[N(CN)_2]_2(pyridine)_2$, by reacting sodium dicyanimide with salts of bivalent transition metals in the presence of pyridine.

G.B. No. 1,067,695 of Tsujikawa and Rembarz et al. Wiss. Z. Univ. Rostock, Math.-Naturwiss. Reihe, 1972, 21(2), 113-117 each discloses the conversion of 2-methyl-4,6-dimethoxy-1,3,5-triazine to 2-methyl-4-methoxy-6-methylamino-1,3,5-triazine.

The major problem encountered in the known reactions is the relatively moderate yield of the coordination complex, zinc bis(imino-bis-carbimic acid methyl ester), and the difficulty in its isolation due to the insolubles present. This limits the yield of aminotriazines obtainable. The Kohler pyridine complex is obtainable in high yields, but its use in the preparation of aminotriazines is not disclosed or suggested.

It has now been found that several novel ligand complexes as well as the metal bis(dicyanimide)bis(pyridine) complex of Kohler can be used in a high yield conversion of metal bis(dicyanimide) to a metal bis(imino-bis-carbimic acid methyl ester) complex. This permits efficient preparation of aminotriazines for use in herbicide production. None of the above cited references disclose the novel metal.dicyanimide.ligand complexes or their use in the quantitative preparation of the metal bis-(imino-bis-carbimic acid methyl ester) complex.

SUMMARY OF THE INVENTION

This invention pertains to a novel intermediate metal dicyanimide ligand complex. The invention further pertains to use of the novel ligand complex in a process for the preparation of aminotriazines in accordance with Reaction Scheme I defined hereinafter. This invention further pertains to a process for the high yield preparation of an intermediate bis(imino-bis-carbimic acid methyl ester), either directly in accordance with Reaction C on Reaction Scheme I, or in situ in accordance with a combination of Reactions B and C on Reaction Scheme I.

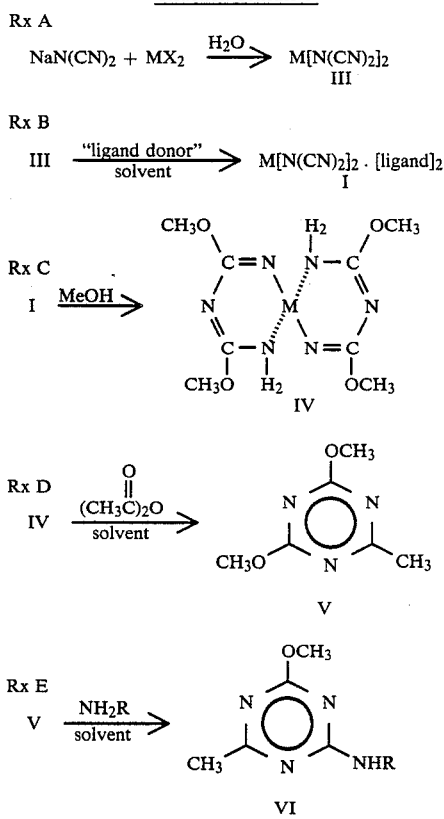

wherein
M is Zn, Cu, Mg, Ca, Fe, Al or Si;
R is H or $C_1$-$C_3$ alkyl;
X is Cl, Br, OAc, $SO_4$, $NO_3$, OH, $PO_4$ or $CO_3$; and
ligand is a group capable of donating a pair of electrons, such as nitrogen or sulfur containing aromatic, aliphatic or heterocyclic compounds or phosphorus containing compounds such as phosphates, phosphites or phosphinic acids.

The novel metal.dicyanimide.ligand complex of the present invention comprises $M[N(CN)_2]_2.[ligand]_2$  I wherein
M is Zn, Cu, Mg, Ca, Fe, Al or Si; and
ligand is a group other than pyridine capable of donating a pair of electrons.

Preferred metals, M, include zinc, magnesium and calcium. Most preferred for use in the present invention is zinc.

Suitable ligands include various groups known as capable of donating a pair of electrons, such as nitrogen or sulfur containing aromatic, aliphatic or heterocyclic groups, or phosphorus containing groups such as phosphates, phosphites or phosphinic acids. Examples of suitable ligands include, but are not limited to, triethylamine, acetonitrile, triphenylphosphine, benzonitrile, N,N-dimethylaniline, acetone, tetrahydrofuran or dimethylsulfoxide. The most preferred ligand is acetonitrile.

The process for the preparation of aminotriazines of the present invention comprises Reactions A through E as summarized above in Reaction Scheme I. This process comprises (a) reacting sodium dicyanimide with a soluble metal salt $MX_2$ wherein M is zinc, copper, magnesium, iron, calcium, aluminum or silicon; and X is chlorine, bromine, acetate, sulfate, nitrate, hydroxide, phosphate, or carbonate; to yield a metallic dicyanimide represented by formula III:

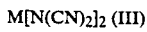

wherein M is defined as above; and (b) reacting the compound of formula III in suitable solvent with a ligand donor capable of donating a pair of electrons to yield of complex of formula I:

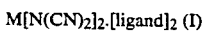

wherein M is defined as above; and ligand is a group capable of donating a pair of electrons; and (c) reacting the complex of formula (I) with methanol to generate a complex of formula IV:

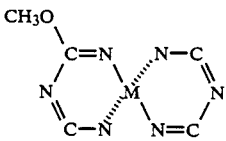

wherein M is defined as above; and (d) reacting the complex of formula IV with a mono- or dicarboxylic acid halide or anhydride to yield a compound of formula V:

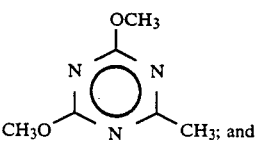

(e) reacting the compound of formula V with an alkylamine of formula $NH_2R$ wherein R is an alkyl group of up to six carbon atoms to yield the desired aminotriazine of formula VI:

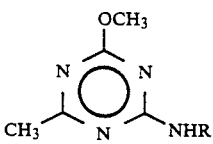

wherein R is as defined above.

This process is preferably used to prepare aminotriazines of formula VI wherein R is methyl. Preferred ligand donors include nitrogen or sulfur containing aromatic, aliphatic or heterocyclic compounds or phosphorus containing compounds such as phosphates, phosphites or phosphinic acids. Examples of such ligand donors include, but are not limited to, pyridine, triethylamine, dimethylsulfoxide, acetonitrile, triphenylphosphine, tetrahydrofuran, acetone, benzonitrile, or N,N-dimethylaniline. Particularly preferred are acetonitrile and pyridine. Suitable metal salts for use herein include those where M is zinc, copper, aluminum or silicon and X is chlorine, bromine, acetate, sulfate, nitrate, hydroxide, phosphate or carboxylate. Preferred is zinc acetate. Preferred metals, M, include zinc, magnesium, calcium and copper. Particularly preferred is zinc, used in combination with acetonitrile as the ligand donor.

This invention further pertains to an in situ process for the high yield preparation of an intermediate bis-(imino-bis-carbinic acid methyl ester) of formula IV

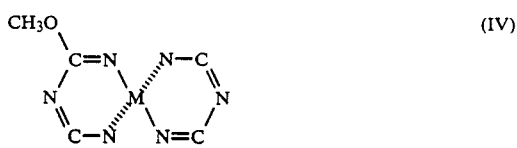

wherein M is zinc, copper, magnesium, Calcium, iron, aluminum or silicon;

comprising reacting a compound of formula III:

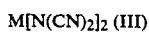

wherein M is defined as above; with a mixture of a ligand donor capable of donating a pair of electrons and methanol to yield the compound of formula IV.

Preferred metals for use in this process are zinc, magnesium, calcium and copper. Preferred ligand donors include nitrogen or sulfur containing aromatic, aliphatic, or heterocyclic compounds or phosphorus containing compounds such as phosphates, phosphites or phosphinic acids. Examples of such ligand donors include, but are not limited to pyridine, triethylamine, dimethylsulfoxide, acetonitrile, triphenylphosphine, tetrahydrofuran, acetone, benzonitrile, or N,N-dimethylaniline. . Particularly preferred are acetonitrile or pyridine used in combination with the metal zinc This invention further pertains to a direct process for the high-yield preparation of an intermediate bis(imino bis-carbinic acid methyl ester) of formula IV

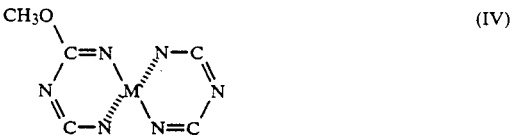

wherein M is zinc, copper, magnesium, calcium, iron, aluminum or silicon; comprising reacting methanol with a complex of formula I:

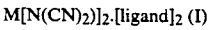

wherein M is as defined above, and ligand is a ligand donor capable of donating a pair of electrons, to generate the desired complex of formula IV.

The preferred metals and ligand donors are as described above for the in the in situ process.

DETAILED DESCRIPTION OF THE INVENTION

The present invention relates to a novel intermediate metal.dicyanimide.ligand complex used in the preparation of aminotriazines. These complexes are useful as intermediates in the preparation of aminotriazines, said aminotriazines being used in the commercial production of herbicides. Thus the complexes of the present invention permit more efficient herbicide production in greater yield at lower costs.

The complexes of formula I are prepared in accordance with Reactions A and B in Scheme I. The metal-dicyanimide.ligand complex is prepared from sodium dicyanimide which is commercially available or readily prepared according to the method of Canadian Patent No. 956,081, which is herein incorporated by reference. The sodium dicyanimide is first reacted with a soluble metal salt in water to form the corresponding metallic bis(dicyanimide) of formula III in accordance with Reaction A on Scheme I.

Suitable metal salts, $MX_2$, for use in Reaction A herein include those wherein M is zinc, copper, magnesium, calcium, iron, aluminum or silicon and X is chlorine, bromine, acetate, sulfate, nitrate, hydroxide, phosphate or carboxylate. Preferred is zinc acetate which can react according to the method of U.S. Pat. No. 2,418,476 of Nagy et al. which is hereby incorporated by reference.

The metallic bis(dicyanimide) of formula III is then converted to the novel metal.dicyanimide.ligand complex of formula I in accordance with Reaction B on Scheme I. Suitable ligand donors include those compounds previously defined as ligands in formula I. The solvent is methanol or a cosolvent of methanol with other suitable solvents, including but not limited to, tetrahydrofuran, acetonitrile, dioxane, N,N-dimethylaniline, triethylamine, pyridine, triphenylphosphine or benzonitrile. Preferred cosolvents include pyridine or acetonitrile. The reaction is conducted at a temperature of from about 20° C. to about 150° C., preferably from about 60° C. to about 80° C., and a pressure of from about 1 to about 5 atmospheres, Preferably at about 1 atmosphere. The ratio of the metallic bis(dicyanimide) of formula III to the ligand donor is from about 1:1 to about 1:20, Preferably from about 1:1 to about 1:4. The reaction is conducted for about 5 to about 50 hours, Preferably for about 10 to about 20 hours.

A further aspect of the present invention is the use of the complexes of formula I in a novel process for the preparation of aminotriazines. The use of the complexes of the present invention or the pyridine complex of Kohler permit preparation of the key intermediate bis-(imino-bis-carbimic acid methyl ester) of formula IV in accordance with Reaction C or Reactions B and C in situ on Scheme I in very high yields. Yields of at least about 80%, typically exceeding about 90%, are obtainable.

A direct process for preparation of the intermediate of formula IV comprises reacting the novel metal.-dicyanimide.ligand complex of formula I, prepared as described above, with methanol to afford in about 100% yield the ester of formula IV This reaction is conducted at reflux temperature, and at a pressure of from about 1 to about 5 atmospheres, preferably at about 1 atmosphere. Alternatively the ester of formula IV may also be prepared from the metallic dicyanimide of formula III by reacting the formula III dicyanamide with the coordinating ligand donor and methanol in an in situ conversion which combines Reactions B and C on Scheme I. It is believed that the donor ligands first convert the metallic dicyanimide to a ligand complex which rearranges in quantitative yield to the bis-carbimic ester of formula IV. Without the ligand it is believed that the dicyanimide of formula III undergoes a disproportionation reaction to an inert form that does not further convert to obtain the aminotriazines. Suitable solvents, reaction temperature, reaction pressure, reaction time, and ratio of the dicyanamide of formula III to the ligand donor are as described above for Reaction B.

These novel processes allow for the direct simple high yield preparation of the bis(imino-bis-carbimic acid methyl ester) of formula IV which is in itself useful as an intermediate for the preparation of aminotriazines. The sequential conversion of the bis(imino-bis-carbimic acid methyl ester) of formula IV to 2-methyl-4,6-dimethoxy-1,3,5-triazine of formula V in Reaction D of Scheme I can be performed by known methods by reaction of the ester of formula IV with aliphatic or cycloaliphatic mono- or dicarboxylic acid halides or anhydrides or with aromatic or heterocyclic mono- or dicarboxylic acid halides or anhydrides at a temperature of between 15° C. and 150° C. Suitable solvents for this reaction include all liquids that do not react with carboxylic acid halides and anhydrides and in which the halide of the metal in question formed as a by-product or the salt of the carboxylic acid in question of the anhydride used for the reaction and of the metal in question are insoluble. Instead of a solvent, an excess of the acid halide or anhydride can be employed. See, for example, Great Britain No. 1,180,346.

The final reaction of 2-methyl-4,6-dimethoxy-1,3,5-triazine of formula V to the desired 2-methyl-4-methoxy-6-alkylamino-1,3,5-triazine of formula VI is conducted in accordance with Reaction E on Scheme I via methods known in the art. The 2-methyl-4,6-dimethoxy-1,3,5-triazine of formula V is reacted with an alkylamine of formula NHR wherein R is an alkyl group of up to six carbon atoms. The reaction is carried out with or without a solvent at a temperature of about 10° C. to 100° C. for several hours. If a solvent is used it can be water, methanol, ethanol, propanol, toluene, methylene chloride, an ether such as dioxane or tetrahydrofuran, or a mixture of two or more of the above. The reaction preferably is carried out under atmospheric pressure if the alkylamine used has a boiling point below 70° C. See, for example, Great Britain No. 1,067,695.

The following examples illustrate the invention but are not intended to limit it in any way. Example 1 utilized the preformed zinc.dicyanimide.pyridine complex of formula I and resulted in a 93.5% yield of bis(imino-bis-carbimic-acid methyl ester) of formula IV. Examples 2-6 were in situ preparations of various dicyanimide ligand complexes and resulted in a range of yields of formula IV compounds of 89.5% to 99%. Example 7 was a control experiment comparing the known dicyanimide to the inventive complex. The control experiment resulted in a lower 75.7% yield of product which required an additional step in the works. Examples 8 and 9 together demonstrate preparation of an aminotriazine from the formula IV intermediate.

EXAMPLE 1

Direct Synthesis of Zinc Bis(imino-bis-carbimic acid methyl ester) from zinc bis(dicyanimide)bis(pyridine)

In a 1 liter round bottom flask was charged 50 g of $Zn[N(CN)_2]_2[pyridine]_2$ and 400 mL methanol. It was heated to reflux and the initial white slurry thinned out and gradually became clear. After overnight reflux, the clear solution was cooled and white crystals were filtered. Weight 37 g. The filtrate was rotovapped under vacuum to give a tan residue which yielded white crystals upon addition of water. The crystals were filtered and combined with above crystals to give 43 g (93.5% yield) of zinc bis(imino-bis-carbimic acid methyl ester).

EXAMPLE 2

In Situ Synthesis of Zinc Bis(imino-bis-carbimic acid methyl ester) from zinc bis(dicyanimide) and pyridine In a 1 liter round bottom flask was charged 50 g $Zn[N(CN)_2]_2$, 40 g pyridine and 500 mL methanol. It was refluxed overnight to form a clear solution. Upon rotovapping under vacuum, an orange residue was formed which was diluted with 700 mL cold water to form white crystals. Upon filtering and drying, a total of 75 g (91% yield) of zinc bis(imino-bis-carbimic acid methyl ester) was obtained.

EXAMPLE 3

In Situ Synthesis of Zinc bis(imino-bis-carbimic acid methyl ester) from zinc bis(dicyanimide) and triethylamine In a 500 mL round bottom flask was charged 20 g zinc bis(dicyanimide), 50 g triethylamine and 300 mL methanol. The reaction mixture was heated to reflux overnight and worked up as described above in Example 2 to yield 32.8 g (99%) zinc bis(imino-bis-carbimic acid methyl ester) and no insoluble by-product.

EXAMPLE 4

In Situ Synthesis of Zinc bis(imino-bis-carbimic acid methyl ester) from zinc bis(dicyanimide) and N,N-dimethylaniline In a 500 mL round bottom flask was charged 20 g zinc bis(dicyanimide), 25 g N,N-dimethylaniline, and 300 mL methanol. It was refluxed overnight and worked up as described above in Example 2 to give 31.8 g (96% yield) zinc bis(imino-bis-carbimic acid methyl ester) and 0.7 g of insoluble by-product.

EXAMPLE 5

In Situ Synthesis of Zinc bis (imino-bis-carbimic acid methyl ester) from zinc bis(dicyanimide) and acetonitrile In a 500 mL round bottom flask was charged 20 g zinc bis(dicyanimide), 100 mL acetonitrile and 250 mL methanol. The reaction was heated to reflux. After overnight reflux, the white slurry thinned out to almost a clear solution. It was cooled to crystallize and filtered. The filter cake was washed with $CH_2Cl_2$ which dissolved all the desired product into the filtrate. The combined filtrate was rotovapped under vacuum to give 32.5 g (98%) zinc bis(imino-bis-carbimic acid methyl ester). The insoluble by-product weighed 0.7 g.

EXAMPLE 6

In Situ Synthesis Of Zinc bis(imino-bis-carbimic acid methyl ester) from zinc bis(dicyanimide) and tetrahydrofuran In a 500 mL round bottom flask was charged 20g zinc bis(dicyanimide), 100 mL tetrahydrofuran and 250 mL methanol. It was heated to reflux overnight and worked up as above in Example 2 to yield 29.5 g (89.5%) zinc bis(imino-bis-carbimic acid methyl ester) and 1.4 g insoluble by-product.

EXAMPLE 7

Synthesis of Zinc bis(imino-bis-carbimic acid methyl ester) from zinc bis(dicyanimide)

In a 500 mL round bottom flask was charged 20 g zinc bis(dicyanimide) and 350 mL methanol. It was heated to reflux overnight and then cooled and filtered. The filtered cake was washed with $CH_2Cl_2$ and filtered. The insoluble by-product weighed 4.7 g (23.5%) and had a strong -CN absorption at 2030 $cm^{-1}$. The combined filtrate was rotovapped under vacuum to product 25 g (75.7% yield) of zinc bis(imino-bis-carbimic acid methyl ester).

EXAMPLE 8

Synthesis of 2-methyl-4.6-dimethoxy-1,3,5-triazine from zinc bis(imino-bis-carbimic acid methyl ester)

A 5-1 flask containing 3 1 acetic anhydride was cooled in an ice bath to 20° C. Then 500 g of zinc bis-(imino-bis-carbimic acid methyl ester) prepared as in Example 7 slowly spooned in an over ½ hour so that the temperature was between 20–25° C. After 10 minutes, a clear solution was formed. For the next 2 hours, the reaction exotherm was controlled by the ice bath to maintain below 35° C. The reaction was stirred overnight at room temperature. The reaction mixture was cooled to 15° C. and filtered. The dried filter cake which was $Zn(OAc)_2$ weighed 273 g (97% recovery). The filtrate was rotovapped with vacuum pump to remove HOAc and $Ac_2O$. The remaining liquid quickly solidified. It was dissolved in 2 1 $H_2O$ and extracted with $2\times1$ 1 $CH_2Cl_2$. Upon stirring 427 g of 2-methyl-4,6-dimethoxy-1,3,5-triazine was obtained. Yield was 89.5%. Further extraction of the aqueous solution with 500 ml $CH_2Cl_2$ recovered another 30 g which brought the yield of 2-methyl-4,6-dimethoxy-1,3,5-triazine to 95.8%.

EXAMPLE 9

Synthesis of 2-methyl-4-methoxy-6-methylamino-1,3,5-triazine from 2-methyl-4.6-dimethoxy-1,3,5-triazine In a 5-1 flask with thermometer, a mechanical stirrer and a water condenser was charged with 427 g of 2-methyl-4,6-dimethoxy-1,3,5-triazine and 2-1 water. It was cooled to 20° C. and then 214 g of 40% $MeNH_2$ was dropped in at room temperature. The clear solution became cloudy when $MeNH_2$ dropped in and gradually became thick after 2 hours of stirring. At this time, liquid chromatography showed complete conversion of 2-methyl-4,6-dimethoxy-1,3,5-triazine to be 99.8% of 2-methyl-4-methoxy-6-methylamino-1,3,5-triazine. It was cooled to 10° C. and filtered. The filtered cake was washed with 1-1 $H_2O$ and dried in an oven at 70° C. overnight. Total weight: 322 g. Yield=75.4% for the first pass. When the filtrate was recycled for the next run, the yield of 2-methyl-4-methoxy-6-methylamino-1,3,5-triazine improved to 92–95% for the next three runs.

What is claimed is:

1. A process for the aminotriazines comprising:
   (a) reacting sodium dicyanimide with a soluble metal salt $MX_2$ wherein M is zinc, copper, magnesium, iron, calcium, aluminum or silicon; and X is chlorine, bromine, acetate, sulfate, nitrate, hydroxide, phosphate, or carbonate; to yield a metallic dicyanimide represented by formula III:

M[N(CN)₂]₂ (III)

wherein M is defined as above; and (b) reacting the compound of formula III in a suitable solvent with a ligand donor capable of donating a pair of electrons to yield of complex of (formula III:

M[N(CN)₂]₂·[ligand]₂ (I)

wherein M is defined as above; and ligand is a group capable of donating a pair of electrons; and (c) reacting the complex of formula (I) with methanol to generate a complex of formula IV:

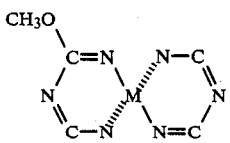

wherein M is defined as above; and (d) reacting the complex of formula IV with a mono- or dicarboxylic acid halide or anhydride to yield a compound of formula V:

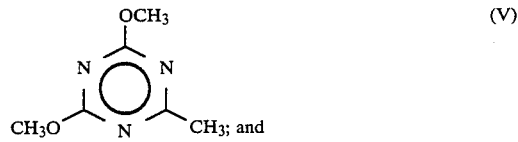

(e) reacting the compound of formula V with an alkylamine of formula NH₂R wherein R is an alkyl group of up to six carbon atoms to yield the desired aminotriazine of formula VI:

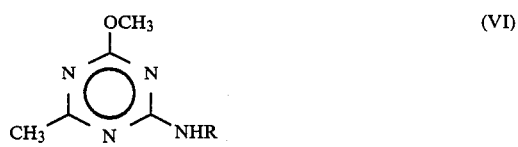

wherein R is as defined above.

2. The process of claim 1 which generate the complex of formula IV in a yield of at least about 80%.

3. The process of claim 1 wherein MX₂ is zinc acetate.

4. The process of claim 1 conducted in a solvent comprising a mixture of methanol and one of tetrahydrofuran, acetonitrile, dioxane, N,N-dimethylaniline, triethylamine, triphenylphosphine or benzonitrile.

5. The process of claim 1 wherein the ligand donor is pyridine, triethylamine, acetone, acetonitrile, triphenylphosphine, dimethylsulfoxide, N,N-dimethylaniline, benzonitrile, or tetrahydrofuran.

6. The process of claim 5 wherein the ligand donor is acetonitrile or pyridine.

7. The process of claim 6 wherein M is zinc, magnesium or calcium.

8. The process of claim 7 wherein the ligand donor is acetonitrile and M is zinc.

9. The process of claim 7 wherein R is CH₃.

10. The process of claim 8 wherein R is CH₃.

* * * * *